United States Patent [19]

Howson

[11] Patent Number: 4,676,776
[45] Date of Patent: Jun. 30, 1987

[54] DEVICE AND METHOD FOR EFFECTING APPLICATION OF A THERAPEUTIC AGENT

[75] Inventor: David C. Howson, Denver, Colo.

[73] Assignee: Intelligent Medicine, Inc., Denver, Colo.

[21] Appl. No.: 692,895

[22] Filed: Jan. 18, 1985

[51] Int. Cl.$^4$ .............................................. A61M 5/00
[52] U.S. Cl. ..................................... 604/31; 604/28; 604/49; 604/51; 604/66; 128/DIG. 12; 128/DIG. 13
[58] Field of Search .................................... 604/48–53, 604/65–67, 80, 93, 95, 119, 121, 154, 246; 128/DIG. 12, DIG. 13

[56] References Cited

U.S. PATENT DOCUMENTS

| | | | |
|---|---|---|---|
| 3,809,871 | 5/1974 | Howard et al. | 604/49 |
| 4,055,175 | 10/1977 | Clemens et al. | 604/66 |
| 4,094,318 | 6/1978 | Burke et al. | 604/65 |
| 4,245,634 | 1/1981 | Albisser et al. | 604/66 |
| 4,280,494 | 7/1981 | Cosgrove, Jr. et al. | 604/66 |
| 4,308,866 | 1/1982 | Jelliffe et al. | 604/67 |
| 4,494,950 | 1/1985 | Fischell | 604/66 |
| 4,498,843 | 2/1985 | Schneider et al. | 604/65 |
| 4,504,263 | 3/1985 | Steuer et al. | 604/65 |
| 4,512,764 | 4/1985 | Wunsch | 604/118 |
| 4,515,584 | 5/1985 | Abe et al. | 604/66 |
| 4,543,955 | 10/1985 | Schroeppel | 604/66 |
| 4,551,133 | 11/1985 | Zegers de Beyl et al. | 604/66 |
| 4,572,189 | 2/1986 | Smith et al. | 128/395 |

FOREIGN PATENT DOCUMENTS 2451424  5/1976  Fed. Rep. of Germany ...... 604/246

OTHER PUBLICATIONS

"A Package of Time Shared Computer Programs for Patient Care" by K. Jelliffe et al, First Annual Symposium on Computer Applications in Medical Care, 10/3/77–10/5/77, Washington D.C.

*Primary Examiner*—Kyle L. Howell
*Assistant Examiner*—David Shay
*Attorney, Agent, or Firm*—Robert E. Harris

[57] ABSTRACT

Device and method are disclosed for effecting application of a therapeutic agent. A removable programmable element is used to control operation of a delivery unit, which unit delivers the therapeutic agent to the patient. The programmable element is programmed, while removed from the delivery unit, by a computer that is operationally independent of the delivery unit to insure the integrity of subsequent delivery of the therapeutic agent to the patient by the delivery unit. The delivery unit requires no microprocessor and can include a plurality of channels for effecting independent delivery of therapeutic agents in each channel under the control of the programmable element. The programmable element is programmed with respect to available protocol information, including patient history, needs and tolerances, as well as therapeutic agent parameters, to thereby establish a flow profile that is customized for a particular patient during each moment of each day. Patient demand for therapeutic agents can also be accommodated with safeguards being included to assure proper dispensing of the demanded agents.

26 Claims, 7 Drawing Figures

DEVICE AND METHOD FOR EFFECTING APPLICATION OF A THERAPEUTIC AGENT

FIELD OF THE INVENTION

This invention relates to device and method for effecting application of a therapeutic agent to a patient.

BACKGROUND OF THE INVENTION

Various devices and methods have been heretofore suggested and/or utilized to control delivery of therapeutic agents, such as drugs or electrical energy, to a patient. In addition, various drive mechanisms have heretofore been suggested and/or utilized to effect metering of therapeutic agents to a patient, and various on-board dedicated controllers have also been heretofore suggested and/or utilized.

While improvements in dedicated, self-contained controllers have heretofore been made and/or suggested, meaningful further improvements have presented a problem, primarily due to space limitations which have become more acute as the desire and/or need for smaller sized devices has increased while, at the same time, the desirability and/or need for elements providing increasingly sophisticated complexity, which often require additional space, has also increased to the emtent that such elements cannot be fitted into this decreasingly available space.

This has resulted in compromises that often have proved to be undesirable, at least in some respects. For example, delivery units capable of delivering therapeutic agents in liquid form and small enough to be worn on the body of a patient must normally now be single-channeled devices, and such devices have normally been limited to delivery of a therapeutic agent at either a controlled rate or a cycled bolus, with the rate being manually adjustable or automatically changed to programmed levels only up to a few times in any twenty-four hour period (with provision being also sometimes made ior a brief supplemental bolus of varying size upon demand by the patient or amplitude release on demand of the patient when combined with a profile of a programmed waveform).

Known systems and methods for programming and controlling delivery units have varied, but generally include a manual knob or pushbutton, or buttons on a keyboard, which adjust parameters, and the values of which may be displayed on a panel.

Ambulatory delivery devices capable of delivering therapeutic agents in liquid form have also been heretofore suggested and/or utilized. Within this category are delivery units that are implanted into the body of a patient. Such devices have been typically passive type devices (such as pressurized medication delivery devices) or have been adapted from cardiac pacemaker technology, and flow profile programs for these units have nornally been communicated telemetrically to the unit by a programmer. Several such emisting devices use the approach of a keyboard remote to the delivery unit, while others use a large, desktop special-purpose computer connected with a telemetry antenna, with such telemetry using pulse-modulated electromagnetic fields.

The programs contained within such dedicated computers are designed with a limited number of pre-programed waveforms. Because of the use of a limited selection of predetermined profiles, these computers are, in effect, an emtension of manual keyboards, and do not give the user either the capability of specifying the profile waveform itself, or of combining freely-defined waveform components. Moreover, these programmers are usually further limited to programming single-chamber devices.

The telemetered programming systems described above use "random access memory" (RAM) units to store the transmitted data in the delivery unit. RAM units, however, have inherent disadvantages, which include the need for sustained power to avoid loss of memory contents, and are designed for ease and speed of writing into memory as well as reading the nemory contents which results in relatively high susceptibility to transient electromagnetic noise.

Such programmable devices most often require the use of microprocessors (which depend upon a separate machine program to operate) as well as a program of user-defined parameters. Changing flow profiles in most of these devices entails rewriting the machine program as well as the user program. The machine progran is, however, not accessible to reprogramming by the user, and the program must therefore be physically replaced since it is normally contained in a "read only memory" (ROM) unit that is incapable of being reprogrammed (or is reprogrammable only after physical removal and special procedures).

In addition, the relative complexity of the machine programs needed for such general-purpose microprocessors does not easily allow unambiguous proof of all possible logical states of the processor. While such proof is possible in theory, it is extremely difficult to demonstrate in reality, and very expensive to implement. Such proof is therefore limited to relatively simple logic networks and programs, that are far below the complexity of the typically-used microprocessor and machine program.

More recently, dual microprocessors have been used to compensate for the failure potential inherent in single-processor designs, in order to assure only safe failure modes. This does not, however, resolve the problem of ambiguity, and creates a trap for logic states not explicitly contained in a truth table used for comparison.

Since known devices use specially designed programming computers, they tend to be very limited in their capability and the difficulty of writing programs for such computers is very high. In addition, known devices provide only the minimum functions needed to program the delivery unit, and do not provide assistive programs or databases.

The status of known devices intended for table or pole mounting, and used with relatively high flow rates, is somewhat different than for ambulatory devices. Such known large-volume delivery units, however, normally provide only constant flow rate profiles or combinations thereof. Also, the controls for such devices are normally local on-board, and are typically of the keyboard variety which are used in conjunction with various data displays. Also typically, currently used devices have microprocessor controls, with the most advanced systems using dual processors for error detection.

In such devices, a plurality of flow channels have been provided. Typically, however, a primary channel is used to supply a fluid which is usually delivered in large volumes, and a secondary channel is used to supply a smaller volume of a drug containing fluid (see, for example, U.S. Pat. No. 4,391,598 to Thompson). In this system, the fluid flow in the primary channel is interrupted only when a manual order is given which also causes conmencement of flow through the secondary channel, and after flow through the secondary channel has occurred at a known flow rate for a time period calculated to be coincident with the emptying of the reservoir associated with the secondary channel, flow is reverted back to the primary channel. In addition, the flow rate in each channel is constant and set by the user with on-board controls.

Another form of multi-channel device has also been suggested in which the flow rate in each channel is a fixed ratio to that of the other channels, depending upon selection of mechanical elements (see, for example, U.S. Pat. No. 3,737,251 to Berman et al).

Another large delivery unit has been suggested which can control up to four flow channels, but utilizes a constant flow rate for each channel that is set using onboard controls.

A single-channel delivery unit has been suggested which has connectors provided for computer access. However, the delivery unit and computer are not designed together as a system. Instead, a user must first provide a computer, and then program the computer for the intended purpose, with conmunication between the delivery unit and computer being effected by direct wire connection.

SUMMARY OF THE INVENTION

This invention provides a system and method for application of one or more therapeutic agents to a patient which overcomes many of the disadvantages of known devices and methods such as set forth hereinabove.

A computer, such as a general purpose computer, is used to program a programmable element remotely from the delivery unit (which can be a pump), and the programmable element, after placement in the delivery unit, controls operation of the delivery unit, which delivery unit may contain a plurality of channels all of which are controlled by the programmable element to effect delivery of a plurality of therapeutic agents.

Through use of this arrangement, the device and method of this invention allows programming of a therapeutic agent delivery unit (single or multi-channel) to deliver virtually any needed or desired flow rate profile, be it physical matter (such as a liquid) or a form of energy (such as electrical), normally as a function of time, with such profiles being definable by the user or selected from a database of profiles that does not require machine modification of the delivery unit. Patient or event triggering capability is also provided to allow introduction of supplemental profiles, which are later automatically terminated and flow returned to control by the programmed profile, and each channel is independently or contingently controllable under fully automatic and unattended operation.

In addition, manual control functions or special profiles assigned by programming may also be provided, and secure, verifiable means of transmission of data from the data entry means to the delivery unit may also be utilized, which transmission means requires neither electrical power to sustain its contents nor continued connection between data entry means and delivery means.

Since the data entry means is based on a general-purpose computer, the difficulty of writing applications software is minimized, and assistive programs are also provided in the data entry means to aid the user in specifying the desired flow profile (including, if desired, graphics-based entry means), and provision can also be made to simulate the action of the delivery unit, both physically and pharmacokinetically. Emtensive error-reduction means, including use of databases for cross-checking drug information, protocol parameters, and patient records may also be provided, and dosage adjustment assistance may be provided based on laboratory blood values by use of pharmacokinetic algorithims (or through the use of special calculators enabling the patient to apply results of test done in the home or other non-laboratory environment) for fine adjustments of the dosage scale.

The system and method of this invention thus permits virtually unlimited programming capabilities without compromising the size and weight of the delivery unit. Conversely, by freeing the system from size constraints, virtually unlimited programming capabilities may be included within the system and yet the delivery unit (which may be worn by the patient) can be smaller than even less sophisticated devices.

This unlimited programming capability, or power, thus provides an ability to program single or multiple channels with each of the multiple channels being capable of having different drugs and individually specified delivery profiles and with the machine code of the delivery unit being automatically programmed for each channel, as well as an ability to assign, by programming, manual or event synchronized input sources to any designated delivery channel.

It is therefore an object of this invention to provide an improved system and method for application of a therapeutic agent to a patient.

It is another object of this invention to provide an improved system and method for application of a therapeutic agent to a patient wherein a programmable logic unit is programmed remote from the delivery unit and then used at the delivery unit for controlling operation of the delivery unit.

It is another object of this invention to provide an improved system and method for application of a therapeutic agent to a patient that allows delivery of any selected flow rate profile with progranming of a programmable logic unit being carried out remotely of the delivery unit and the delivery unit being virtually free of size restraints other than being adapted to receive the progranmable logic unit.

It is still another object of this invention to provide an improved system and method for application of a therapeutic agent to a patient wherein a programmable logic unit is used to individually control operation of a plurality of channels in the delivery unit.

With these and other objects in view, which will become apparent to one skilled in the art as the description proceeds, this invention resides in the novel construction, combination, arrangement of parts and method substantially as hereinafter described and more particularly defined by the appended claims, it being understood that changes are meant to be included as come within the scope of the claims.

DESCRIPTION OF THE DRAWINGS

The accompanying drawings illustrate a complete embodiment of the invention according to the best mode so far devised for the practical application of the principles thereof and in which.

DESCRIPTION OF THE INVENTION

Figure 1:
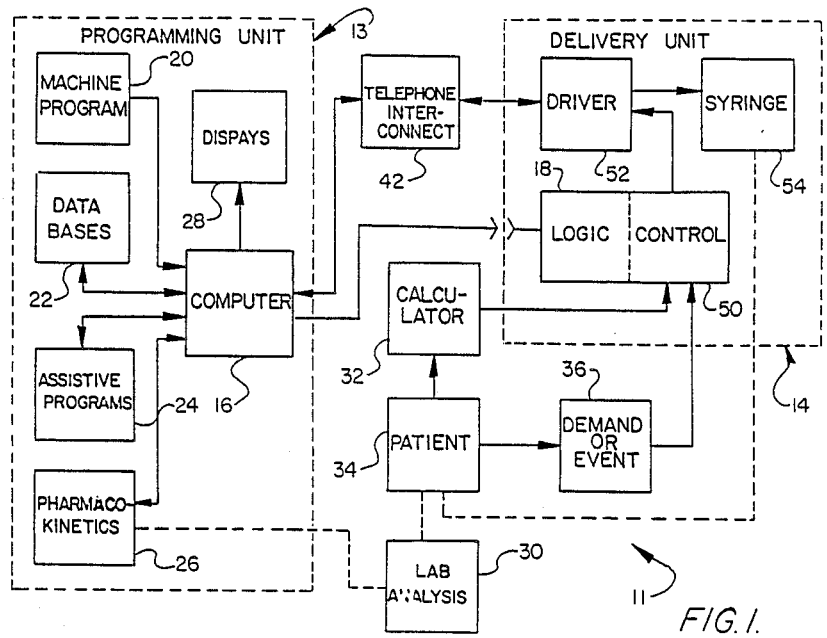
FIG. 1 is a block diagram of the device of this invention with patient interaction being also indicated.

The block diagram of FIG. 1 summarizes the interconnection the components, or elements, of the device of this invention. As shown, device 11 includes, primarily, a programming unit 13 and a delivery unit 14.

programming unit 13 includes a computer 16, preferably a general-purpose computer, that is capable of programming programmable logic unit 18 used to control operation of delivery unit 14 when placed in delivery unit 14 (as indicated in FIG. 1). As also indicated in FIG. 1, by way of emample, computer 16 has machine program 20 connected therewith, as well as databases 22, assistive programs 24 and pharmacokinetic programs 26, as needed, for programming the logic unit.

Obviously, computer 16 could also have connected therewith any number of other input devices, such as a keyboard, graphics, tablet, joystick, "mouse", or other manipulanda, or other data acquisition devices. In addition, computer 16 can also be connected with one or more displays 28, which, by way of emample, could be a video screen, a liquid crystal display, a printer and/or or a plotter.

Logic unit 18 is preferably a programmable logic cartridge. Programmable logic cartridge 18 may be any form of non-volatile logic (meaning the programmed form will be retained in the absence of electrical power) or otherwise volatile logic sustained by an accompanying power source, such as a small back-up battery. Preferred forms or such components include, but are not meant to be limited to, commercially available devices such as programmable read only memories (PROMs), erasable programmable read only memories (EPROMs), electrically erasable programmable read only memories (EEPROMs), electrically alterable programmable read only memories (EAPROMs), nonvolatile random access memories (NVRAMs), and programmable logic arrays (PLAs).

The logic cartridge contains the configurable portion of the logic path of the control unit and establishes operation thereof depending upon the contained configuration of logic gates or states in the delivery unit. Program 20 is a machine program that is used to operate computer 16, and the system transforms the user-provided information into a logic configuration suitable for operating the delivery unit in accordance with the intended delivery requirements of the user. Computer 16 then writes the configuration into logic cartridge 18 and automatically verifies correct entry.

Figure 2:
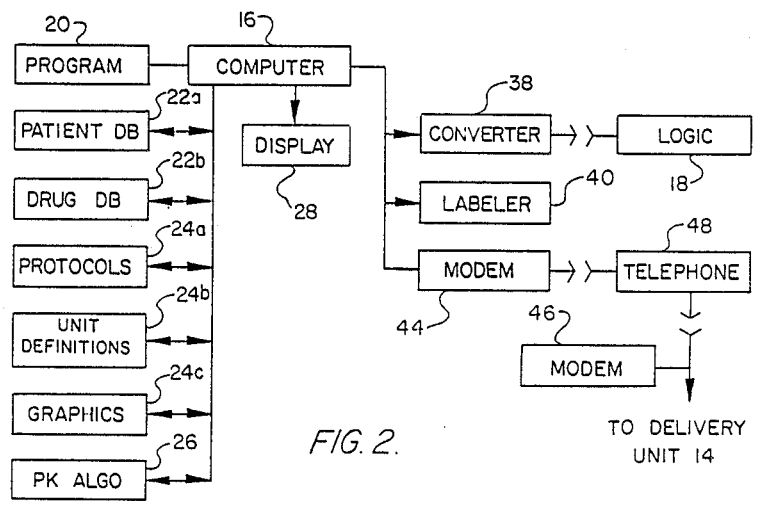
FIG. 2 is an expanded block diagram of the programming unit shown in FIG. 1.

In assisting the user to enter error-free information, the computer uses appropriate databases 22 and assistive programs 24 to determine inconsistencies, to offer the user supporting information and/or to aid calculations, as indicated in greater detail in FIG. 2. Databases 22 can therefore include, by way of example, patient DBs 22a and drug DBs 22b. These can be augmented by assistive programs 24 (such as protocols 24a, unit definitions 24b, and graphics 24c), and by pharmacokinetic algorithms 26 to thereby provide information such as accepted drug dosage ranges, interactions between drugs when present in the patient at the same time, and parameters for mathematical dose-response or pharmacokinetic models for each drug.

By using these databases and assistive programs, the computer is able to automatically interpolate from the preferred nomenclature of the user and units of measurement to those needed by the logic of the delivery unit (heretofore, the user was required to perform numerous calculations before being able to adjust a delivery unit, each such calculation carrying a finite probability of introducing error).

The computer is also able to utilize the databases to retain the history of the individual patient's treatment and responses, and the patient's pertinent physiological or other parameters used to assist determination of safe and effective dosage. Furthermore, the computer uses a "library" of delivery protocols, either provided by the manufacturer, developed by the user, or provided by a third party. Such protocols assist the user by requiring only the minimum amount of data needed to correctly adjust the dosage to an individual patient.

The computer may also use pharmacokinetic, pharmacodynamic, or dose-response models (designated generally by the numeral 26 in FIGS. 1 and 2), to either aid programming of the delivery profile of the delivery unit, or to simulate the outcome of a profile in terms of resulting bodily concentrations of the delivered substances, or both. Furthermore, such programs may aid the user in finally adjusting dosages after taking requirements of substance concentrations within the body of the patient at some time intervals after beginning delivery. Such data may be acquired from a clinical setting, such as a hospital laboratory 30, as generally indicated in FIG. 1, or in the patient's own normal surroundings by means of simplified tests.

Data may then be entered into the programming computer for programming a new logic cartridge, or may be communicated to the delivery unit. In the latter case, the logic cartridge contains sections of configurable logic suitably different from the base configurations so as to allow small changes in effective dosage rates from the base program.

The suitable interpolation of a concentratron measurement to a logic configuration or selection is normally automatically accomplished in the programming computer, but may be accomplished by a calculator 32 (operated by patient 34) which has the ability to communicate with the delivery unit under special circumstances such as, for example, in response to patient perception of clinical symptoms.

As brought out more fully hereinafter, a patient, or an event, is also able to initiate delivery of the therapeutic agent, as generally indicated in FIG. 1 by the block entitled demand or event 36, the output from which is coupled to delivery unit 14.

As also indicated in FIG. 2, data is written into logic cartridge 18 by computer 16 through converter 38, with the computer also providing, if desired, an output to labeler 40 (which provides a suitable label for attachment to the logic cartridge). As also indicated in FIG. 2, computer 16 may also be connected with delivery unit 14 through a telephone interconnect system 42 that includes modems 44 and 46 at opposite sides of telephone system 48, for purposes as described more fully hereinafter.

Delivery unit 14 includes a control unit 50 which receives removable programmable logic unit 18. Control unit 50 drives a driver 52, which driver, in turn, controls operation of an applicator, such as a syringe 54, through which the therapeutic agent is delivered to patient 34. Delivery unit 14 will not operate if logic unit 18 is removed from control unit 50.

The driver mechanism may be of any suitable form, and may be, for example, a mechanism that depresses the plunger of a syringe, as is now preferred, with all components contacted by the fluid drug formulation being preferably disposable.

Figure 3:
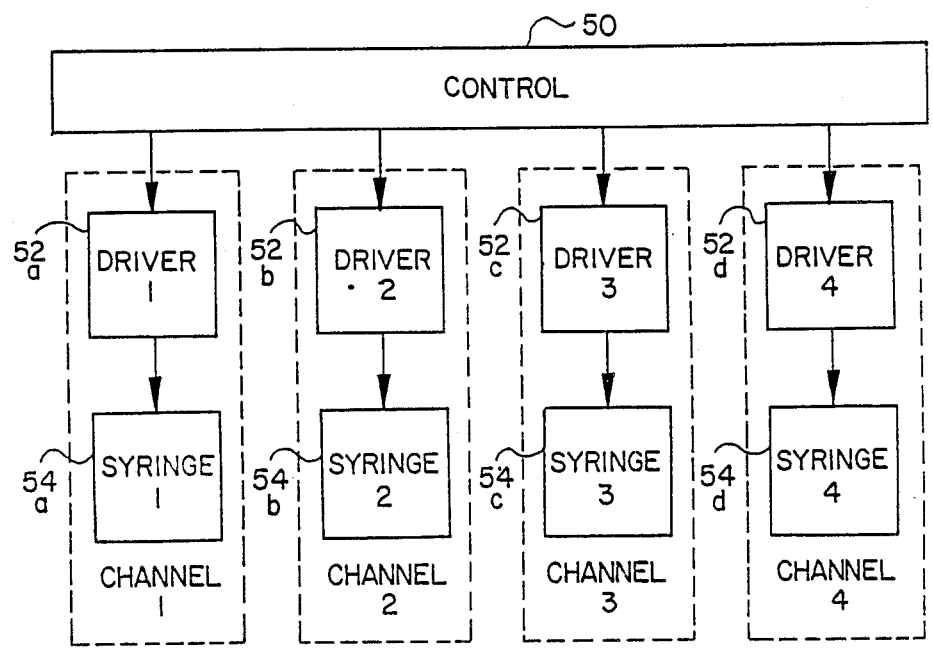
FIG. 3 is a block diagram of the delivery unit, similar to that shown in FIG. 1, but illustrating use of the control a unit to control plurality of channels through which therapeutic agents may be delivered to a patient.

The delivery unit may contain a plurality of independently controlled fluid delivery channels as indicated in FIG. 3. When so utilized, control unit 50 independently controls each driver (indicated by the numerals 52a–d in FIG. 3), and each driver controls a separate syringe (indicated by the numerals 54a–d in FIG. 3) with each driver and syringe establishing separate channels indicated in FIG. 3 as channels 1-4).

The preferred embodiment uses a modular design assembly in which any number from one to four channels may be used at any one time. More than one delivery unit assembly may, however, be synchronized together for applications requiring more than four fluid channels.

In its preferred form, the controller logic consists of discrete logic elements so as to make up a state machine. This state machine performs strict sequences of logic functions depending upon the state of a clock or other control element, or a combination thereof, and upon the state of the logic programmed into the logic cartridge. Alternately, combinational logic can be utilized in a dedicated control machine, which again uses the configurable logic in the programmable cartridge to define the sequence of logic operations.

While the intended preferred embodiment of this invention utilizes a delivery unit without a microprocessor, the delivery unit could include a suitably programmed microprocessor (or microprocessors), which reads operating parameters from the information contained in the programmable memory cartridge which is programmed remote from the delivery unit.

The electronic controller 56 of control unit 50 also utilizes a read/write memory 58 (see FIG. 4) within the delivery unit to record data about the actual operating history over a time period, for emample, a number of days, and can include coding of date and time of day, if desired. Such data are useful for various purposes, including diagnosing hardware problems, recording data of patient-demanded delivery events, recording data on physiologically -or blood-level-controlled delivery profiles, and/or compiling data on the patient's compliance with a prescribed delivery schedule.

Figure 4:
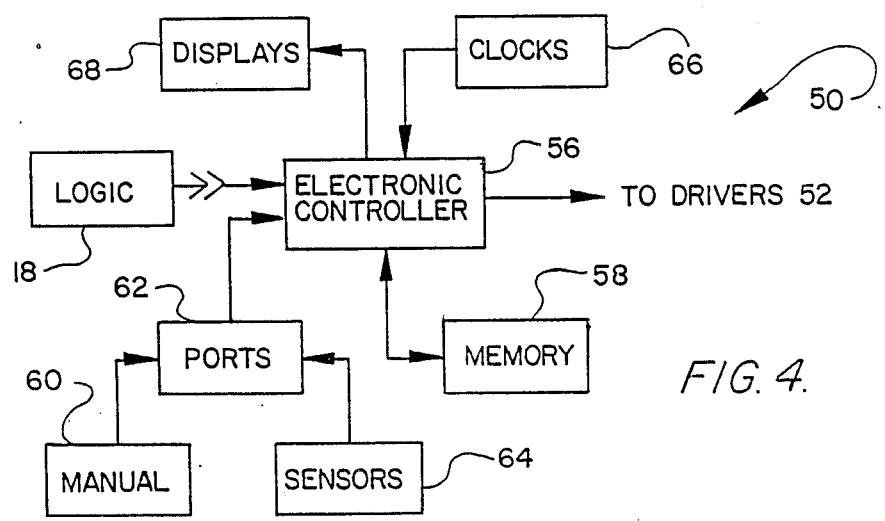
FIG. 4 is an expanded block diagram of the control unit shown in FIG. 1.

The delivery unit may, depending upon the application, use manually-operated controls 60 (connected through ports 62 to controller 56 as indicated in FIG. 4) to synchronize delivery events of any complexity with the detailed waveform and amplitude information relating to the events being programmed into the logic cartridge. Such manual controls may operate any of the available channels, the assignment being made by appropriately programming the logic cartridge.

Similarly, delivery events may be synchronized by detecting, as by sensors 64 as indicated in FIG. 4, the occurrence of a physiological event or by appearance of a critical level of a substance in the blood or other physiological fluid. Of greater complexity, the profile of fluid delivery over time may change in accordance with direct modulation from the detected levels and/or statistical behavior of physiological events, or from detected levels of substances in the blood or other physiological fluids.

The computer can also communicate with the delivery unit remotely by means of the telephone interconnect unit 42. In this case, communication is normally restricted to hardware problems diagnosis, routinely report patient usage information, or to slightly adjust dosage rate.

As also shown in FIG. 4, control unit 50 includes electronic controller 56 capable of dividing time into time segments, such as, for example, one-minute intervals, utilizing clocks 66. Typically, clocks 66 follows a twenty-four hour clock in real time. At each time segment, the controller addresses the logic cartridge and performs a series of housekeeping checks, then looks to see if a delivery event is scheduled.

Since the computer programs the logic cartridge, the computer preferably uses programs that translate the user's expression of delivery profile into time-encoded series of discrete delivery pulses. Mathematically, the programs encode a combination of both pulse-width modulated and pulse-period modulated trains of delivery events. The computer then synthesizes a flow profile using relatively rapid trains of pulses.

Figure 5:
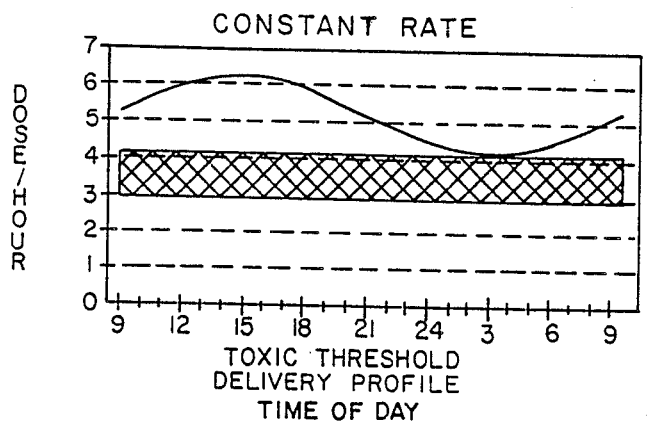
FIG. 5 is a graph illustrating a typical constant rate profile for therapeutic agent delivery during a one day period.
Figure 6:
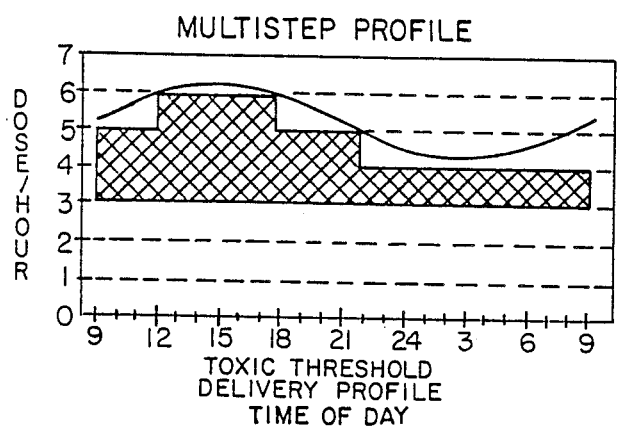
FIG. 6 is a graph illustrating a typical multilevel approximation to the toxicity limit for therapeutic agent delivery during a one day period.
Figure 7:
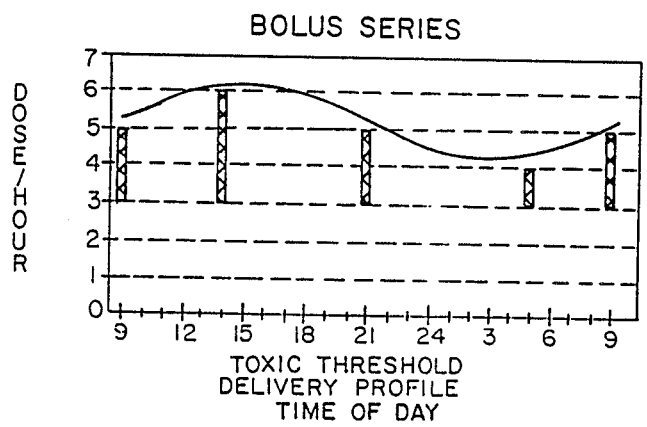
FIG. 7 is a graph illustrating a typical series of boli (discrete shots) of therapeutic agent delivery spaced over a one day period and illustrating limitations in dose rate due to varying toxic susceptibility.

Emamples of some of the more simple profiles are shown in FIGS. 5, 6 and 7. In these examples, the wavelike top line represents an exemplary toxicity limit of a patient which limit varies with a twenty-four hour rhythm. The objective of optimizing flow rate is achieved by delivering the therapeutic agent at a rate which comes close to the toxic limit, but never exceeds it.

FIG. 5 shows a typical constant rate profile deliverable by many delivery systems now known, and FIG. 6 shows a typical multilevel approximation to toxicity limit, while FIG. 7 shows the results of a typical series of boli (discrete volumes) spaced variably in time and limited in dose content by the varying toxic susceptibility.

The delivery unit is not dependent upon the size or type of mechanical drive being used. The controller would work just as well with a small capacity element, such as, for example, a 0.1 cc/day capacity, as with a large capacity element, such as, for example, a 2000 cc/day capacity driver element. It would also work equally as well with other drive mechanisms, such as, for example, a pulsatile solenoid drive or a continuous-flow proportional regulator, as with the syringe drive.

Since the computer designs the delivery profile for each channel, based on the specifications of the user, not only can each channel be made to operate independently, the channels can also be linked in operation relative to one another to allow greater operating flexibility. For example, while a particular delivery unit might offer up to four channels of 30 cc of a therapeutic agent each, two channels are operated in series or in tandem, the result is to allow 60 cc capacity for a particular therapeutic agent (such as a relatively insoluble drug, for example).

Of major importance is the fact that this capability has been designed without requiring microprocessors in the controller. While microprocessors are powerful, they may have several significant limitations, including higher costs, limited availability, and software provability limitations (at least without use of multiple units to provide a cross-check).

All of the "intelligent" features are included in the programming unit. This allows the delivery unit (which is the key component in the patient's view) to be kept simple, have a low cost, and yet be highly reliable. If desired, however, the delivery unit can provide displays (such as displays 68 connected with controller 56 as indicated in FIG. 4).

The programming unit is far more powerful and friendly than known systems, which attempt to fit sophisticated controls into small size and thus conpromise both size and user friendliness. In addition, the system of this invention, uses partitioning (i.e., programming in a separate unit from that of the delivery unit) which is a major departure from known practice.

The programming unit prompts the user (such as a pharmacist) for patient and prescription data. Basic protocol information may be requested from a database to speed data entry. The protocol outline asks only for the minimum amount of data needed to individualize dosages to the patient.

Protocols are derived from published sources, third parties, or are developed by the user. In the latter case, friendly software is preferably provided to assist the user by asking a series of questions. All protocol entries and changes may be preferably date/time coded to provide a complete audit trail.

If requested, the computer queries a drug database to check for dosage range errors and for compliance with package insert labeling. It also checks for possible adverse drug interactions. The user may over-ride certain types of warnings by providing signature for the audit trail held in the pernanent patient record.

The provided software may, if desired, cause the computer to look up the patient's history on the patient database to check for consistency. Again, the user may over-ride certain warnings with appropriate security precautions. The patient's records are automatically updated upon the users verification of correct entry.

The computer can be used not only to nanage each of the infused drugs, but other drugs as well. It also charts the responses of the patient to therapy, or any laboratory measurements.

The computer is thus utilized as far more than just a delivery unit programmer. It is a conprehensive medication nanagement system. The user can also ask the computer to use pharmacokinetic algorithms to help derive optimum profiles for a patient. The algorithm prompts for laboratory data and may, if requested, remind the user of the correct sampling protocol.

When the user indicates program acceptance, the computer writes the data into the logic cartridge and automatically verifies its contents against the original image. If desired, the computer can cause a label to be printed, in appropriate pharmacy form, for placement on the cartridge. Finally, the computer may cause a hard copy of the patient's updated record to be printed, and copies all data into the patient database.

The programmable logic cartridge is a nonvolatile memory (it does not lose contents with power loss). It may be used either as a one-time disposable, or as a reprogrammbale cartridge. The former provides relatively low cost with ultimate data security. Disposability assures the least chance of a mixup, which is possible with re-use. The old cartridges may be included in the patient's permanent physical file for medico-legal backup.

Although microprocessor-based devices use read-only memories, they use them for the microcode of the processor, and not for the user program—which is in the random-access memory (RAM) unit with presently known systems. In addition, known systems, despite containing one or two microprocessors, have only a very limited "vocabulary" of permissible flow profiles. To change the profile, the machine microcode must be rewritten, which is quite difficult and cannot normally be done by the user. Such systems are therefore rigidly limited in capability despite the use of relatively complex computing chips which are required to manage these very simple functions, with most of the sophistication of such a process being used to manage manual controls and displays.

Unlike the more commonly used RAM unit which is designed for high-speed writing as well as reading at low voltages and is thus relatively susceptible to electrical noise as well as being volatile, the logic cartridge used in this invention is exceedingly resistant to environmental electromagnetic noise.

Most significantly, the logic memory unit is used as a configurable logic, and not as a simple table of parameters to be looked up. This gives the system of this invention enhanced programming power.

As can be appreciated from the foregoing, this invention provides an improved system and method for application of a therapeutic agent to a patient.

What is claimed is:

1. A device for effecting application of a therapeutic agent to a patient, said device comprising:
    delivery means adapted to deliver a preselected therapeutic agent to a patient and having a controllable element for controlling therapeutic agent flow from said delivery means; and
    electronic means for controlling said controllable element and including a pre-programmed removable logic cartridge means providing sole operative memory for said device with said logic cartridge means being substantially operationally nonvolatile to thereby provide programmable means in a format capable of implementing complex flow profiles of substantial duration for said delivery means when said programmable means is operatively positioned at said device.

2. The device of claim 1 wherein said delivery means includes a syringe, and wherein said controllable element includes a driver for driving said syringe.

3. The device of claim 1 wherein said delivery means has a plurality of channels for separately conveying therapeutic agent therethrough, wherein said controllable element includes a controllable unit each of which is associated with a different one of said channels, and wherein said programmable means is pre-programmed to effect a separate flow profile for each of said channels.

4. A device for effecting application of a therapeutic agent to a patient, said device comprising:

drive means for controlling delivery of a preselected therapeutic agent to a patient;

electronic means including a removable programmable logic cartridge means providing sole operative memory for said drive means with said logic cartridge means being substantially operationally non-volatile to thereby provide programmable means in a format capable of implementing complex flow profiles of substantial duration to control operation of said drive means when said programmable logic cartridge is programmed and operatively positioned; and computer means for receiving said removable programmable logic cartridge and programming the same with a then selected flow profile based upon predetermined parameters of patient need and therapeutic agent capabilities.

5. The device of claim 4 wherein said programmable logic cartridge is selected from one of a programmable read-only-memory, an erasable programmable read-only-memory, an electrically erasable read-only-memory, an electrically alterable read-only-programmable memory, a non-volatile random access memory, and a programmable logic array.

6. The device of claim 4 wherein said computer means is a general-purpose computer.

7. The device of claim 4 wherein said device has a plurality of channels for separately delivering therapeutic agent to a patient, and wherein said drive means includes a driver associated with each of said channels, with each of said drivers being controlled by said programmable logic cartridge, and with said programmable logic cartridge being programmed by said computer to effect a separate flow profile for each of said channels.

8. A device for effecting application of a therapeutic agent to a patient, said device comprising:

application means including delivery means adapted to deliver a preselected therapeutic agent to a patient with said delivery means having a controllable element for controlling the flow of said therapeutic agent from said delivery means, and said application means also including electronic means for controlling said controllable element with said electronic means including a removable logic cartridge means providing sole operative memory for said application means with said logic cartridge means being substantially operationally non-volatile to thereby provide programmable means in a format capable of implementing complex flow profiles of substantial duration for said delivery means when said programmable means is programmed and operatively positioned at said application means; and programming means operationally independent of said application means for programming a then selected flow profile into said programmable means while said programmable means is removed from said application means to thereby enhance the integrity of said then selected flow profile during subsequent use while operatively positioned at said application means.

9. The device of claim 8 wherein said application means includes a syringe, and wherein said controllable element includes a driver for driving said syringe.

10. The device of claim 8 wherein said logic cartridge is a read-only-memory type device.

11. The device of claim 8 wherein said logic cartridge is one of a programmable read-only-memory, an erasable programmable read-only-memory, an electrically erasable programmable read-only-memory, an electrically alterable progranable read-only-memory, a non-volatile random access memory and a programmable logic array.

12. The device of claim 8 wherein said programming means is a general-purpose computer.

13. The device of claim 12 wherein said device includes program means connected with said computer to provide data-base and assistive programs so that said computer is responsive to patient and drug information, as well as protocol and unit definition information when programming said programmable means.

14. The device of claim 8 wherein said programmable means is programmed by said programming means to cause said flow through said delivery means to deliver said therapeutic agent by one of a time-based and an event-synchronized flow profile.

15. The device of claim 14 wherein said therapeutic agent is one of physical matter and energy, and wherein said flow profile controls delivery of said selected therapeutic agent.

16. The device of claim 8 wherein said delivery means includes channel means defining a plurality of channels for separately delivering therapeutic agent, wherein said controllable element includes a plurality of controllable units each of which is associated with a different one of said channels, wherein said programmable means controls each of said controllable units, and wherein said programming means programs said programmable means so that each of said units operates independently of one another whereby independent flow profiles are established for each of said channels.

17. The device of claim 8 wherein said application means includes a controller and memory means connected with said controller for recording the history of therapeutic agent flow from said device.

18. A method for effecting application of a therapeutic agent to a patient, said method comprising:

providing delivery means adapted to deliver a preselected therapeutic agent to a patient; controlling operation of said delivery means through electronic means that includes a removable logic cartridge that provides sole operative memory for said application means with said logic cartridge being substantially operationally non-volatile to thereby provide a programmable element in a format capable of implementing complex profiles of substantial duration so that so programmable element, when operatively positioned, establishes the flow profile of said delivery means; and pre-programming said programmable element while removed from said application means.

19. The method of claim 18 wherein said method includes providing a syringe and a driver for driving said syringe in order to deliver therapeutic agent to said patient.

20. The method of claim 18 wherein said method includes programming said logic cartridge while removed from said delivery means by use of a general-purpose computer.

21. The method of claim 18 wherein said method includes providing a delivery means having a plurality of channels through which therapeutic agents are separately conveyed for delivery to a patient and separately controlling the flow of therapeutic agent through each of channels by said programmable element by pre-programming said programmable element to establish a separate flow profile for each of said channels.

22. A method for effecting application of a therapeutic agent to a patient, said method comprising:
   determining the parameters of flow for a preselected therapeutic agent with respect to a predetermined patient;
   programming a logic cartridge that provides sole operative memory for said application of said therapeutic agent with said logic cartridge being substantially operationally non-volatile to thereby provided a programmable element in a format capable of implementing complex profiles of substantial duration so that said programmable element establishes a flow profile according to the determined parameters of flow for said preselected therapeutic agent; and
   using said programmable element to control flow of said predetermined therapeutic agent to said patient.

23. The method of claim 22 wherein said method includes determining the parameters of flow for a plurality of preselected therapeutic agents with respect to a predetermined patient, programming said programmable element with a flow profile according to the determined parameters of flow for each of said preselected therapeutic agents, and using said programmable element to separately control flow of said preselected therapeutic agents to said patient.

24. The method of claim 22 wherein said method includes using a computer to determine said flow parameters.

25. The method of claim 24 wherein user needs and patient history are utilized in said computer to determine said parameters.

26. The method of claim 25 wherein said flow profile is established based upon the toxic threshold of said patient at preselected times of the day to thereby enhance the effectiveness of therapeutic agent delivery to said patient.

* * * * *

UNITED STATES PATENT AND TRADEMARK OFFICE
CERTIFICATE OF CORRECTION

PATENT NO. : 4,676,776

DATED : June 30, 1987

INVENTOR(S) : David C. Howson

It is certified that error appears in the above-identified patent and that said Letters Patent is hereby corrected as shown below:

Column 1, line 7, between "to" and "device", insert --a--.

Column 1, line 27, "emtent" should be --extent--.

Column 1, line 40, "ior" should be --for--.

Column 1, line 58, "emisting" should be --existing--.

Column 1, line 68, "emtension" should be --extension--.

Column 2, line 12, "nemory" should be --memory--.

Column 2, line 20, "progran" should be --program--.

Column 4, line 6, "Emtensive" should be --Extensive--.

Column 4, line 49, "progranmable" should be --programmable--.

UNITED STATES PATENT AND TRADEMARK OFFICE
CERTIFICATE OF CORRECTION

PATENT NO. : 4,676,776

DATED : June 30, 1987

INVENTOR(S) : David C. Howson

It is certified that error appears in the above-identified patent and that said Letters Patent is hereby corrected as shown below:

Column 5, line 26, "progranming" should be --programming--.

Column 5, line 33, "emample" should be --example--.

Column 6, line 56, "concentratron" should be --concentration--.

Column 7, line 29, "indicated" should be --(indicated--.

Column 7, line 57, "emample" should be --example--.

Column 8, line 38, "Emamples" should be --Examples--.

Column 9, line 1, before "two" insert --when--.

Column 9, line 21, "conpromise" should be --compromise--.

Column 9, line 25, "najor" should be --major--.

UNITED STATES PATENT AND TRADEMARK OFFICE
CERTIFICATE OF CORRECTION

PATENT NO. : 4,676,776
DATED : June 30, 1987
INVENTOR(S) : David C. Howson

It is certified that error appears in the above-identified patent and that said Letters Patent is hereby corrected as shown below:

Column 9, line 43, "pernanent" should be --permanent--.

Column 9, line 50, "nanage" should be --manage--.

Column 9, line 56, "nanagement" should be --management--.

Column 12, line 5, "progranable" should be --programmable--.

Column 12, lines 30 and 31, "programable" should be --programmable--.

Column 13, line 13, "provided" should be --provide--.

Signed and Sealed this

Twenty-third Day of August, 1988

Attest:

DONALD J. QUIGG

Attesting Officer     Commissioner of Patents and Trademarks